(12) United States Patent
Triebel

(10) Patent No.: US 11,583,582 B2
(45) Date of Patent: *Feb. 21, 2023

(54) USE OF RECOMBINANT LAG-3 OR THE DERIVATIVES THEREOF FOR ELICITING MONOCYTE IMMUNE RESPONSE

(71) Applicant: IMMUTEP, Orsay (FR)

(72) Inventor: Frederic Triebel, Versailles (FR)

(73) Assignee: IMMUTEP, Saint-Aubin (FR)

( * ) Notice: Subject to any disclaimer, the term of this patent is extended or adjusted under 35 U.S.C. 154(b) by 102 days.

This patent is subject to a terminal disclaimer.

(21) Appl. No.: 16/274,466

(22) Filed: Feb. 13, 2019

(65) Prior Publication Data
US 2019/0175726 A1    Jun. 13, 2019

Related U.S. Application Data

(60) Division of application No. 15/407,864, filed on Jan. 17, 2017, now Pat. No. 10,232,038, which is a continuation of application No. 12/681,068, filed as application No. PCT/IB2008/002653 on Oct. 3, 2008, now Pat. No. 9,579,382.

(30) Foreign Application Priority Data

Oct. 5, 2007  (EP) ..................... 07291214

(51) Int. Cl.
| | | |
|---|---|---|
| A61K 38/17 | (2006.01) | |
| A61K 38/19 | (2006.01) | |
| A61K 45/06 | (2006.01) | |
| A61K 31/337 | (2006.01) | |
| A61K 31/704 | (2006.01) | |
| A61K 39/39 | (2006.01) | |
| A61K 31/7068 | (2006.01) | |
| C07K 16/00 | (2006.01) | |
| C07K 14/705 | (2006.01) | |
| A61K 39/00 | (2006.01) | |
| C07K 16/30 | (2006.01) | |

(52) U.S. Cl.
CPC ............ *A61K 39/39* (2013.01); *A61K 31/337* (2013.01); *A61K 31/704* (2013.01); *A61K 31/7068* (2013.01); *A61K 38/1774* (2013.01); *A61K 39/0011* (2013.01); *A61K 45/06* (2013.01); *C07K 14/70503* (2013.01); *C07K 16/00* (2013.01); *C07K 16/30* (2013.01); *A61K 2039/54* (2013.01); *A61K 2039/545* (2013.01); *A61K 2039/55516* (2013.01); *A61K 2039/57* (2013.01); *A61K 2039/585* (2013.01); *C07K 2317/24* (2013.01); *C07K 2317/732* (2013.01); *C07K 2319/00* (2013.01); *C07K 2319/40* (2013.01)

(58) Field of Classification Search
CPC .......... C07K 14/70503; C07K 2319/00; A61K 38/1774; A61K 39/39; A61K 2039/57; A61P 37/04; A61P 35/00
See application file for complete search history.

(56) References Cited

U.S. PATENT DOCUMENTS

| | | |
|---|---|---|
| 5,539,084 A | 7/1996 | Geysen |
| 5,700,907 A | 12/1997 | Hercend et al. |
| 5,773,578 A | 6/1998 | Hercend et al. |
| 5,785,973 A | 7/1998 | Bixler et al. |
| 5,798,231 A | 8/1998 | Hercend et al. |
| 5,817,511 A | 10/1998 | Hercend et al. |
| 5,830,758 A | 11/1998 | Hercend et al. |
| 5,840,839 A | 11/1998 | Wang et al. |
| 5,874,250 A | 2/1999 | Hercend et al. |
| 5,955,300 A | 9/1999 | Faure et al. |
| 5,976,877 A | 11/1999 | Hercend et al. |
| 6,114,516 A | 9/2000 | Hercend et al. |
| 6,143,273 A | 11/2000 | Faure et al. |
| 6,277,368 B1 | 8/2001 | Hiserodt et al. |
| 6,410,509 B1 | 6/2002 | Triebel |
| 6,482,925 B1 | 11/2002 | El Tayar et al. |
| 6,596,536 B1 | 7/2003 | Hercend et al. |
| RE38,313 E | 11/2003 | Faure et al. |
| 6,855,802 B1 | 2/2005 | Triebel et al. |
| 6,875,844 B1 | 4/2005 | Ronsin et al. |
| 7,109,026 B2 * | 9/2006 | Triebel .................. A61P 35/00 435/455 |
| 7,294,712 B2 | 11/2007 | Hercend et al. |
| 2002/0192195 A1 | 12/2002 | Triebel |
| 2004/0081686 A1 | 4/2004 | Kravtzoff et al. |

(Continued)

FOREIGN PATENT DOCUMENTS

| | | |
|---|---|---|
| CA | 2391927 A1 | 5/2001 |
| EP | 0252741 A2 | 1/1988 |

(Continued)

OTHER PUBLICATIONS

Clinical Trial Study NCT00349934 (version 1), IMP321 Phase I Breast Carcinoma, first posted on Jul. 10, 2006.*
Shapiro et al., Lymphocyte activation gene 3: a novel therapeutic target in chronic lymphocytic leukemia, Haematologica, 102(5): 874-882. (Year: 2017).*
2005 FDA Guidance for Industry Estimating the Maximum Safe Starting Dose in Initial Clinical Trials for Therapeutics in Adult Healthy Volunteers, total pages: 30 (Year: 2005).*
Clinical Trial Study NCT00351949 (version 2), posted on Oct. 23, 2006). (Year: 2006).*
Extended European Search Report dated Mar. 27, 2019 in European Patent Application No. 18 20 8378.2.
Woo, S. et al., "Immune inhibitory molecules LAG-3 and PD-1 synergistically regulate T cell function to promote tumoral immune escape", Cancer Research, Dec. 20, 2011, vol. 72, No. 4, pp. 917-927.

(Continued)

*Primary Examiner* — Hong Sang
(74) *Attorney, Agent, or Firm* — Scully, Scott, Murphy & Presser, P.C.

(57) ABSTRACT

The present invention relates to the use of a recombinant LAG-3 or derivatives thereof in order to boost a monocyte-mediated immune response, in particular to elicit an increase in the number of monocytes in blood. This finds use in the development of novel therapeutic agents for the treatment of an infectious disease or cancer.

11 Claims, 6 Drawing Sheets

(56) References Cited

U.S. PATENT DOCUMENTS

| | | |
|---|---|---|
| 2004/0171551 A1 | 9/2004 | Triebel |
| 2008/0003235 A1 | 1/2008 | Triebel |
| 2008/0069770 A1 | 3/2008 | Hercend et al. |
| 2009/0130054 A1 | 5/2009 | Jooss et al. |
| 2013/0309250 A1 | 11/2013 | Cogswell et al. |
| 2016/0310570 A1 | 10/2016 | Triebel |
| 2018/0271940 A1 | 9/2018 | Triebel et al. |

FOREIGN PATENT DOCUMENTS

| | | |
|---|---|---|
| EP | 2 044 949 A1 | 4/2009 |
| JP | 2006-124383 A | 5/2006 |
| JP | 2006-141346 A | 6/2006 |
| WO | 96/40210 A1 | 12/1996 |
| WO | WO 98/23741 A1 | 6/1998 |
| WO | WO 98/23748 A1 | 6/1998 |
| WO | 01/035989 A3 | 5/2001 |
| WO | 2005/035779 A2 | 4/2005 |
| WO | WO 2005/103079 A1 | 11/2005 |
| WO | 2008/156712 A1 | 12/2008 |
| WO | 2009/044273 A2 | 4/2009 |

OTHER PUBLICATIONS

Blackburn, S.D. et al., "Coregulation of CD8 T cell exhaustion by multiple inhibitory receptors during chronic viral infection", Nature Immunology, Nov. 30, 2008, vol. 10, No. 1, pp. 29-37.
Extended European Search Report dated Nov. 13, 2019 issued in European Patent Application No. 19189911.1.
Albert R. K., et al., "The Merck Manual of Diagnosis and Therapy 18th Edition", Merck Research Labratories, pp. 1161-1167 (2006).
Fougeray, S. et al., "A soluble LAG-3 protein as an immunopotentiator for therapeutic vaccines: Preclinical evaluation of IMP321", Vaccine, (2006), vol. 24, pp. 5426-5433.
Bukowski et al., J. Clin. Oncol., 1994, 12:97-106.
Bock et al., Cancer Res. 1991, 51, 2649-2654.
2005 FDA Guidance for Industry Estimating the Maximum Safe Starting Dose in Initial Clinical Trials for Therapeutics in Adult Healthy Volunteers.
Suntharalingam, G. et al., "Cytokine Storm in a Phase 1 Trial of the Anti-CD28 Monoclonal Antibody TGNa412", The New England Journal of Medicine, vol. 355, pp. 1018-1028 (2006).
Brignone, C. et al., "A Soluble Form of Lymphocyte Activation Gene-3 (IMP321) Induces Activation of a Large Range of Human Effector Cytotoxic Cells", The Journal of Immunology vol. 179, pp. 4202-4211 (2007).
Principles of cancer therapy; The Merck Manual of Diagnosis and Therapy, 18th Edition, p. 1164, tables 149-2 (2006).
Casati Chiara et al, Soluble Human LAG-3 Molecule Amplifies the In vitro Generation of Type I Tumor-Specific Immunity. Cancer Research; 2006, 66(8): 4450-4460.
Miller et al., Paclitaxel plus bevacizumab versus paclitaxel alone for metastatic breast cancer. The New England Journal of Medicine; 2007, 357(26): 2666-2676.
Huard et al. "Characterization of the major histocompatibility complex class II binding site on LAG-3 protein", Proc. Natl. Acad. Sci. USA, vol. 94, pp. 5744-5749, May 1997.
Triebel "LAG-3: a regulator of T-cell and DC responses and its use in therapeutic vaccination", TRENDS in Immunology. vol. 24 No. pp. 619-622, Dec. 2003.
Brignone et al., "A Phase I Pharmacokinetic and Biological Correlative Study of IMP321, a Novel MHC Class II Agonist, in Patients with Advanced Renal Cell Carcinoma", Clin Cancer Res 2009; 15:6225-6231, Sep. 2009.
Brignone et al., "First-line chemoimmunotherapy in metastatic breast carcinoma: combination of paclitaxel and IMP321 (LAG-31g) enhances immune responses and antitumor activity", Journal of Translational Medicine 2010.
Riott et al., Immunology, Fourth Edition, 1996, Mosby, p. 7.9-7.11.
Lee et al., J. Immunol., 1999, 163-6292-6300.
Kirkin et al., 1998, APMIS, 106: 665-679.
Chaux et al., Int J Cancer, 1998, 77: 538-542.
Boon, Adv Can Res, 1992, 58: 177-210.
Brignone, C. et a.,"IMP321 (sLAG-3) Safety and T Cell Response Potentiation Using An Influenza Vaccine As A Model Antigen: A Single-Blind Phase I Study," Vaccine, vol. 25, 2007; pp. 4641-4650.
Prigent, Philippe, et al.; "Lymphocyte Activiation Gene-3 Induces Tumor Regression And Antitumor Immune Responses;" Eur. J. Immunol., vol. 29, No. 12, Dec. 1, 1999; pp. 3867-3876.
Triebel F. et al., "Lag-3, A novel lymphocyte activation gene closely related to CD4", J. Exp. Med., (1990), 171, pp. 1393-1405.
Brignone C. et al., "IMP321 (sLAG-3), an immunopotentiator for T cell responses against a HBsAg antigen in healthy adults: a single blind randomised controlled phase I study", Journal of Immune Based Therapies and Vaccines, (2007), 5:5, 15 pages.
Pinto A C et al., "Schedule Treatment Design and Quantitative In Vitro Evaluation of Chemotherapeutic Combinations for Metastatic Prostate Cancer Therapy", Cancer Chemother Pharmacol 67:275-284 (2011).
Pollaro L. et al., "Strategies to Prolong the Plasma Residence Time of Peptide Drugs", Med. Chern. Commun. 1:319-324(2010).
U.S. non-Final Office Action dated Dec. 14, 2022 received in U.S. Appl. No. 16/918,527.

\* cited by examiner

USE OF RECOMBINANT LAG-3 OR THE DERIVATIVES THEREOF FOR ELICITING MONOCYTE IMMUNE RESPONSE

TECHNICAL FIELD

The present invention relates to the use of recombinant LAG-3 or derivatives thereof in order to boost a monocyte-mediated immune response.

It enables an increase in monocyte numbers in blood.

It finds many applications in particular in the development of novel therapeutic agents in cancer immunotherapy.

In the description which follows, the references between brackets [ ] refer to the attached reference list.

STATE OF THE ART

The lymphocyte activation gene 3 (hlag-3) expressed in human CD4+ and CD8+ activated T cells as well as in activated NK cells encodes a 503 amino acids type I membrane protein (LAG-3) with four extracellular immunoglobulin superfamily (IgSF) domains [1]. A murine lymphocyte activation gene 3 (mlag-3) was cloned and approximatively 70% of homology was found with hlag-3, with the same proline rich motif in the intracytoplasmic tail.

LAG-3 (CD223), described as being a natural high affinity ligand for MHC class II, is known to induce maturation of monocyte-derived dendritic cells in vitro, and is used as an immunotherapy adjuvant to induce CD4 T helper type 1 responses and CD8 T cell responses in vivo [2]. Further information regarding LAG-3 and its use as an immunostimulant may be found in TRIEBEL et al. [1], TRIEBEL et al. [3], and HUARD et al. [4].

Some forms of soluble LAG-3 can bind to MHC class II molecules and can induce dendritic cells to mature and migrate to secondary lymphoid organs where they can prime naïve CD4-helper and CD8-cytotoxic T cells leading to tumour rejection [5].

More recently a recombinant soluble human LAG-3Ig fusion protein (IMP321) was shown to activate a large range of effector cells in both innate and acquired immune responses, for example inducing monocytes-macrophages to secrete cytokines/chemokines [6].

Monocytes are produced by the bone marrow from haematopoietic stem cell precursors called monoblasts. They constitute between three to eight percent of the leukocytes in the blood. Monocytes circulate in the bloodstream for about 24 hours (half-life of 8 hours) and then typically move into tissues throughout the body. In the tissues, monocytes mature into macrophages, epithelioid cells or antigen-presenting cells (APCs, for example dendritic cells). Monocytes are responsible for phagocytosis (ingestion) of foreign substances in the body. Monocytes can perform phagocytosis using intermediary (opsonising) proteins such as antibodies or complement that coat the pathogen, as well as by binding to the pathogen directly via pattern-recognition receptors that recognize pathogens. Monocytes are also capable of killing infected host cells via antibody, termed antibody-dependent cell-mediated cytotoxicity (ADCC). Due to their secretion and phagocytosis properties, monocytes-macrophages occur in a specific and specific immune response.

The study of membrane markers allows the identification of monocyte populations, mature or not, dystrophic or not. The molecules present on monocyte membranes, mature or not, are almost always non specific but correspond to the following activities:

receptor for the Fc fragment of IgG (CD16, CD32, CD64),
receptor for the Fe fragment of IgE (CD23),
receptor for complement fractions (CD11b, CD21/CD35),
leukocyte adhesion proteins (CD11a, CD11c),
protein facilitating binding to LPS of Gram-bacteria (CD14),
protein with tyrosine phosphatase activity (CD45).

DISCLOSURE OF THE INVENTION

The authors of the present invention have now discovered, entirely unexpectedly, that human LAG-3 or derivatives thereof when inoculated into patients with highly malignant tumors, for example patients with metastatic breast cancer (MBC) or metastatic renal clear-cell carcinoma (MRCC), induced a potent immunity which is monocyte dependent.

Said induced immunity manifests itself by a significant increase in blood monocyte counts.

This result was achieved by means of plural administration of LAG-3 or derivatives thereof to patients receiving immunotherapy or chemo-immunotherapy.

This result is rather surprising since binding to, and activation of, monocytes is not expected to be followed by monocyte expansion. Indeed monocytes are end-of-differentiation hematopoietic cells and can not proliferate. They can stay in the blood as monocytes or differentiate toward either macrophages or dendritic cells under the influence of different cytokines, until they die. Thus it is believed, without limitation to the following theory, that the mechanism of action involved may be a proliferative signal directed to hematopoietic precursor cells (before the promonocyte stage) residing in the bone marrow, or an increase in the half-life or residence time of mature circulating monocytes.

Therefore the present invention relates to the use of a recombinant LAG-3 protein or derivative thereof that elicits monocyte mediated immune response, for the manufacture of a medicament inducing an increase in monocyte numbers for the treatment of an infectious disease or cancer.

By "derivatives of LAG-3", in the sense of the present invention, is meant mutants, variants and fragments of LAG-3 provided that they maintain the ability of LAG-3 to bind MHC class II molecules.

Thus, the following forms of LAG-3 may be used:
the whole LAG-3 protein,
a soluble polypeptide fragment thereof consisting of at least one of the four immunoglobulin extracellular domains, namely the soluble part of LAG-3 comprised of the extracellular region stretching from the amino acid 23 to the amino acid 448 o the LAG-3 sequence disclosed in French patent Application FR 90 00 126,
a fragment of LAG-3 consisting of substantially all of the first and second domains,
a fragment of LAG-3 consisting of substantially all of the first and second domains or all of the four domains, such as defined in WO 95/30750,
a mutant form of soluble LAG-3 or a fragment thereof comprising the D1 and D2 extracellular domains and consisting of:
a substitution of an amino acid at one of the following positions:
position 73 where ARG is substituted with GLU,
position 75 where ARG is substituted with ALA or GLU,
position 76 where ARG is substituted with GLU, or a combination of two or more of those substitutions,
a substitution of an amino acid at one of the following positions:
position 30 where ASP is substituted with ALA,
position 56 where HIS is substituted with ALA,
position 77 where TYR is substituted with PHE,
position 88 where ARG is substituted with ALA,
position 103 where ARG is substituted with ALA,
position 109 where ASP is substituted with GLU,
position 115 where ARG is substituted with ALA,
or a deletion of the region comprised between the position 54 and the position 66,
or a combination of two or more of those substitutions.

Those mutants are described by HUARD et al. (Proc. Natl. Acad. Sci. USA, 11: 5744-5749, 1997).
a physiological variant of LAG-3 comprised of the soluble 52 kDa protein containing D1, D2 and D3.
a recombinant soluble human LAG-3Ig fusion protein (IMP321), a 200-kDa dimer produced in Chinese hamster ovary cells transfected with a plasmid encoding for the extracellular domain of hLAG-3 fused to the human IgG1 Fc.

By «medicament», in the sense of the present invention, is meant an effective plurality of doses of a recombinant LAG-3 protein or derivative thereof.

By «effective plurality of doses of a recombinant LAG-3 protein or derivative thereof», in the sense of the present invention, is meant a formulation that allows administration of one dose of a recombinant LAG-3 protein or derivative thereof every one to several weeks for at least 12 weeks, and preferably for at least 24 weeks, separated by 13-day±2 days administration-free intervals. Advantageously, the administration is an every-two-week schedule.

By «one dose of a recombinant LAG-3 protein or derivative thereof», in the sense of the present invention, is meant a formulation that allows one administration in the range of 0.25-30 mg, preferably 1-6.25 mg, more preferably 6-30 mg, and for example about 1.25 mg of recombinant LAG-3 protein or derivative thereof to a patient in need thereof having a body mass index (weight/height$^2$) in the range of 18-30 kg/m$^2$.

The recombinant LAG-3 or derivatives thereof are administered in a free form, for example in a soluble form by inoculating them systemically, for example as a subcutaneous, intramuscular or intravenous injection, preferably as a subcutaneous injection.

Said recombinant LAG-3 or derivatives thereof may also be formulated so as to allow administration with a compound having anti-cancer or anti-infectious disease immunotherapeutical or chemotherapeutical properties.

By "administration with a compound", in the sense of the present invention, is meant an administration of a recombinant LAG-3 or derivative thereof before, with, or subsequent to, the administration of said compound.

By "compound having anti-cancer or anti-infectious disease chemotherapeutical properties", in the sense of the present invention, is meant for example a chemotherapy agent selected from the group consisting of taxanes (paclitaxel, docetaxel), gemcitabine and anthracyclines (doxorubicine) or an anti-viral agent such as ribavirin.

In a particular embodiment of the invention, recombinant LAG-3 protein or derivative thereof is administered to patients after the first administration of the cytotoxic compound having anti-cancer or anti-infectious disease chemotherapeutical properties.

Advantageously, recombinant LAG-3 protein or derivative thereof is administered to patients is administered 12 to 96 hours after the administration of the cytotoxic compound having anti-cancer or anti-infectious disease chemotherapeutical properties.

In another embodiment, recombinant LAG-3 protein or derivative thereof is administered to patients is administered one or two days after the first administration of the compound having anti-cancer or anti-infectious disease chemotherapeutical properties.

In another particular embodiment of the invention, recombinant LAG-3 protein or derivative and the cytotoxic compound having anti-cancer or anti-infectious disease chemotherapeutical properties are administered simultaneously, separately or sequentially.

Advantageously, in this particular embodiment of the invention, recombinant LAG-3 protein or derivative thereof is administered at least six times, for example seven times, ten times, twelve times or more.

Advantageously, in this particular embodiment of the invention, recombinant LAG-3 protein or derivative thereof is administered on an every-two-week schedule.

Advantageously, recombinant LAG-3 protein or derivative thereof is administered at a dose comprised between 0.25 to 30 mg, eventually at a dose comprised between 6 to 30 mg, eventually at a dose comprised between 8 to 25 mg, eventually between 12 and 20 mg.

By "compound having anti-cancer or anti-infectious disease immunotherapeutical properties", in the sense of the present invention, is also meant for example a compound selected from the group consisting of therapeutic antibodies killing tumour cells through ADCC (antibody-dependent cell cytotoxicity), and mixtures thereof, and preferably from the group consisting of rituximab, cetuximab, edrecolomab, and trastuzumab.

In a particular embodiment of the invention, recombinant LAG-3 protein or derivative thereof and therapeutic antibodies are administered to patients simultaneously, separately or sequentially.

Advantageously, in a particular embodiment of the invention, recombinant LAG-3 protein or derivative thereof is administered to patients the same day as therapeutic antibodies.

The present invention also relates to kit-of-parts, i.e. a combined preparation, containing recombinant LAG-3 protein or derivative thereof and a therapeutic antibody for simultaneous, separate or sequential use.

Advantageously, the kit-of-parts contains recombinant LAG-3 protein or derivative thereof and a therapeutic antibody selected from the group consisting of rituximab, cetuximab, edrecolomab, and trastuzumab.

Preferentially, the kit-of-part of the invention contain recombinant LAG-3 protein or derivative thereof and rituximab.

In the kit-of-parts of the invention, recombinant LAG-3 protein or derivative thereof and a therapeutic antibody form a functional unity, because of a synergistic cytotoxic effect between the two components.

This effect is a new joint effect, because the two components administered alone does not have the same effect as when administered as a combined preparation.

The present invention also relates to kit-of-parts, i.e. a combined preparation, containing recombinant LAG-3 protein or derivative thereof and a compound having anti-cancer or anti-infectious disease chemotherapeutical properties for simultaneous, separate or sequential use.

Advantageously, the kit-of-parts contains recombinant LAG-3 protein or derivative thereof and a compound having anti-cancer or anti-infectious disease chemotherapeutical properties selected from the group consisting of taxanes (paclitaxel, docetaxel), gemcitabine and anthracyclines (doxorubicine).

The present invention also relates to a method for treating a pathological condition involving a monocyte mediated immune response, comprising administering the medicament as above defined to a patient in need thereof.

By "pathological condition involving a monocyte mediated immune response", in the sense of the present invention, is meant viral infectious diseases, parasitic infectious diseases, bacterial infectious diseases, and cancer.

Other advantages may also appear to one skilled in the art from the non-limitative examples given below, and illustrated by the enclosed figures.

EXAMPLES

Example 1: Monocytes Increase in Metastatic Breast Cancer (MBC) Patients Using Low IMP321 Dose Five MBC patients, receiving chemotherapy known to induce tumour cell apoptosis, each received one subcutaneous IMP321 dose of 0.25 mg 1-2 days after chemotherapy every other week, for 24 weeks, separated by 14-day administration-free intervals.

Blood samples were collected in heparinated lithium tubes (Vacutainer; BD Biosciences) from each patient, 14 days after the last IMP321 injection (i.e. looking at lasting immunomodulatory effects of the product), at 3 months (Day 85) and 6 months (Day 170). PBMCs were isolated on Ficoll-Paque gradient (Pharmacia) using LeucoSep tubes (Greiner Bio-One), and used immediately.

The increase in number of monocytes was analysed by fluorescence-activated cell sorting (FACS) in said fresh PBMC samples (because monocytes are sensitive to freezing), and compared with the monocyte counts carried out on fresh PBMC samples collected before IMP321 administration (Day 1).

Figure 1:
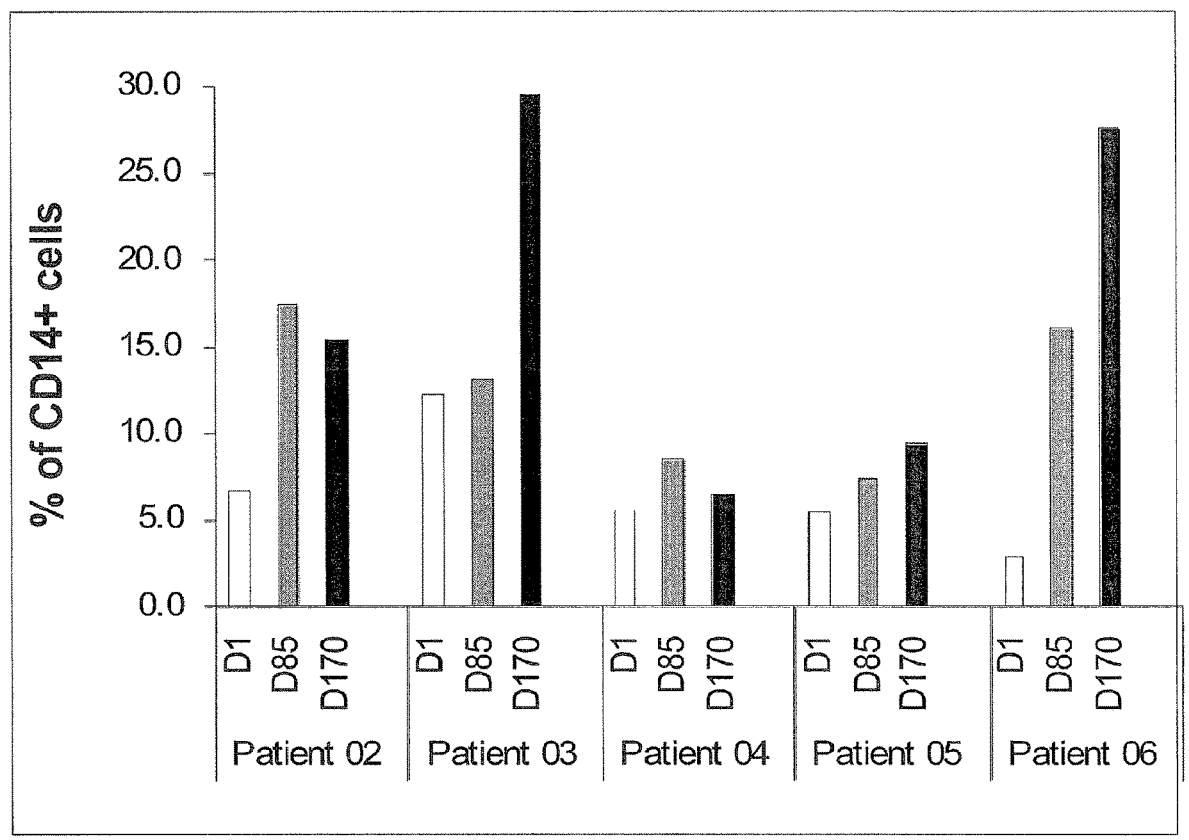
FIG. 1 represents fluorescence-activated cell sorting (FACS) analysis of monocytes (i.e. $CD14^+CD45^+$ cells) in PBMCs from from metastatic breast carcinoma patients.

The results are represented in FIG. 1.

The results showed a 2.5-fold (at 3 months, Day 85) and a 3.5-fold (at 6 months, Day 170) mean increase of monocyte counts at this low IMP321 dose clinical protocol.

In order to confirm the above results, a more direct and probably more accurate approach was carried out, which was to quantify directly ex-vivo the number of monocytes in whole blood (i.e. without prior purification of PBMCs on Ficoll gradient) by first measuring the exact volume of blood to be analyzed with diluted fluorescent beads and then counting the number of $CD14^+$ cells (i.e. monocytes) in the gated $CD45^+$ (leukocytes) cells present in this whole blood volume.

Figure 2:
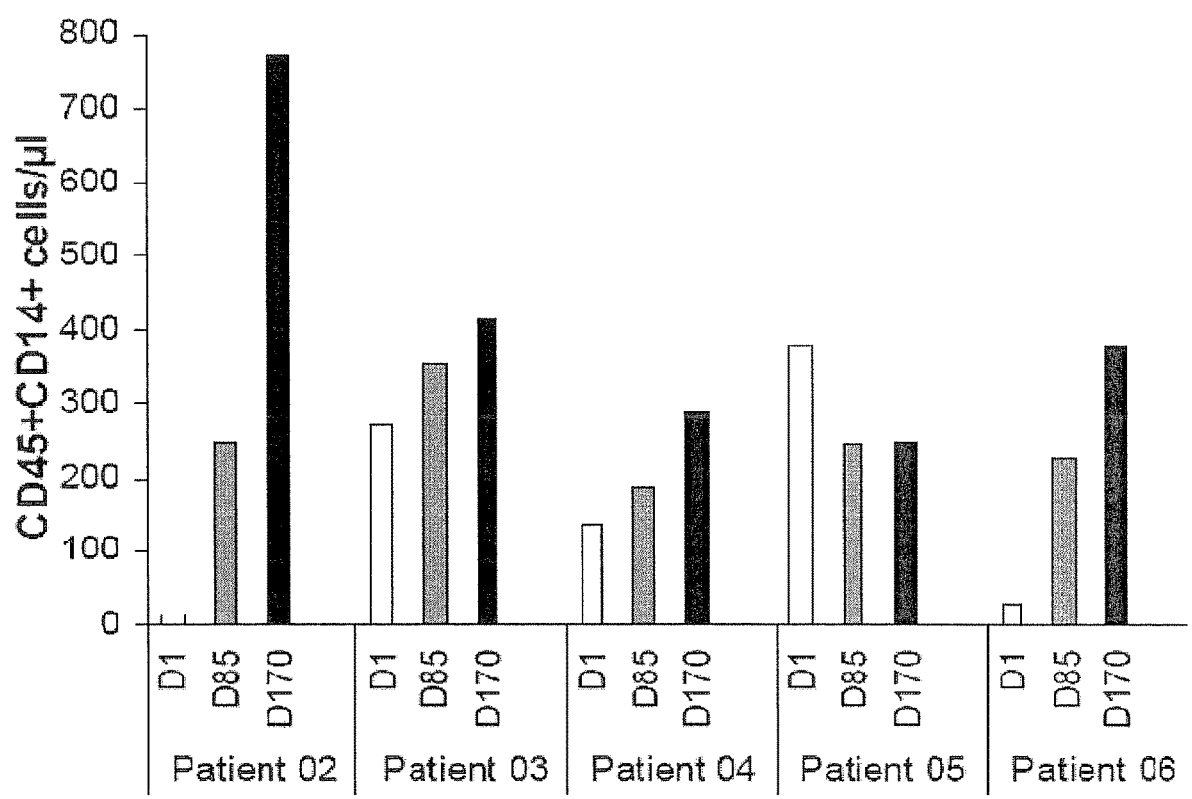
FIG. 2 represents fluorescence-activated cell sorting (FACS) analysis of monocytes (i.e. $CD14^+CD45^+$ cells) in fresh whole blood from metastatic breast carcinoma patients.

The results are represented in FIG. 2.

The results showed a 4.4-fold mean increase at Day 170 (2.8-fold at Day 85) when IMP321 was given at low dose (0.25 mg) for a long period of time, 6 months, with 12 injections, showing strong and direct stimulation of the targeted MHC class $II^+$ monocyte-like hematopoietic cells.

Example 2: Monocytes Increase in Metastatic Renal Clear-Cell Carcinoma (MRCC) Patients Using High IMP321 Dose Three MRCC patients each received one subcutaneous IMP321 dose of 6.25 mg every other week, for 12 weeks, separated by 14-day administration-free intervals.

Blood samples were collected as described above from each patient, days after the last IMP321 injection (i.e. looking at lasting immunomodulatory effects of the product), at 2 months (Day 57) and 3 months (Day 85), and used immediately.

The expansion of $CD14^+CD45^+$ cells was analysed by FACS in fresh blood samples (because monocytes are sensitive to freezing), and compared with the monocyte counts carried out on fresh blood samples collected before IMP321 administration (Day 1).

Figure 3:
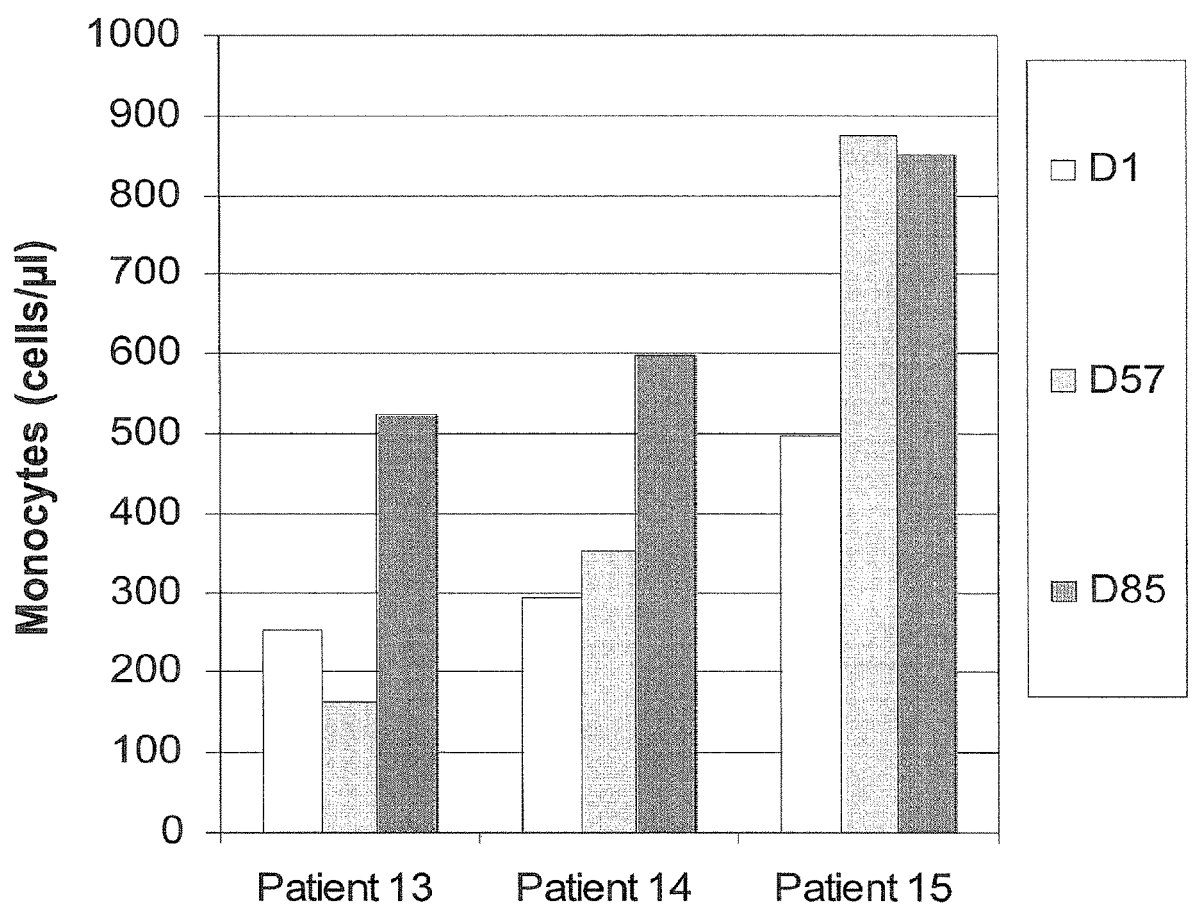
FIG. 3 represents fluorescence-activated cell sorting (FACS) analysis of monocytes (i.e. $CD14^+CD45^+$ cells) in fresh whole blood from metastatic renal cell cancer patients.

The results are represented in FIG. 3.

The results showed a 2-fold (at 3 months, Day 85) mean increase of monocyte counts with this high IMP321 dose clinical protocol where patients received only 6 injections.

Example 3: Monocytes Increase in Metastatic Breast Carcinoma Patients Receiving Paclitaxel and IMP321 Doses Patients receiving as a first line chemotherapy for metastatic breast carcinoma 6 cycles of paclitaxel (80 mg/m$^2$ given i.v.) on days 1, 8, and 15 of a 28 day cycle, received 1-30 mg s.c. (sub-cutaneous) IMP321 on days 2 and 16 of each 28-day cycle. Alternatively, IMP321 was administered at days 3 or 17.

Accordingly, each patient received a standard 6-month course of weekly paclitaxel with 12 s.c. injections of IMP321, each injection being given one to two days after paclitaxel administration on an every-two-week schedule.

The increase in absolute monocyte counts per microliter of fresh blood was analysed by fluorescence-activated cell sorting (FACS), 14 days after the last injection, at 3 months (Day 85) and 6 months (Day 170) compared to day 1.

Figure 4:
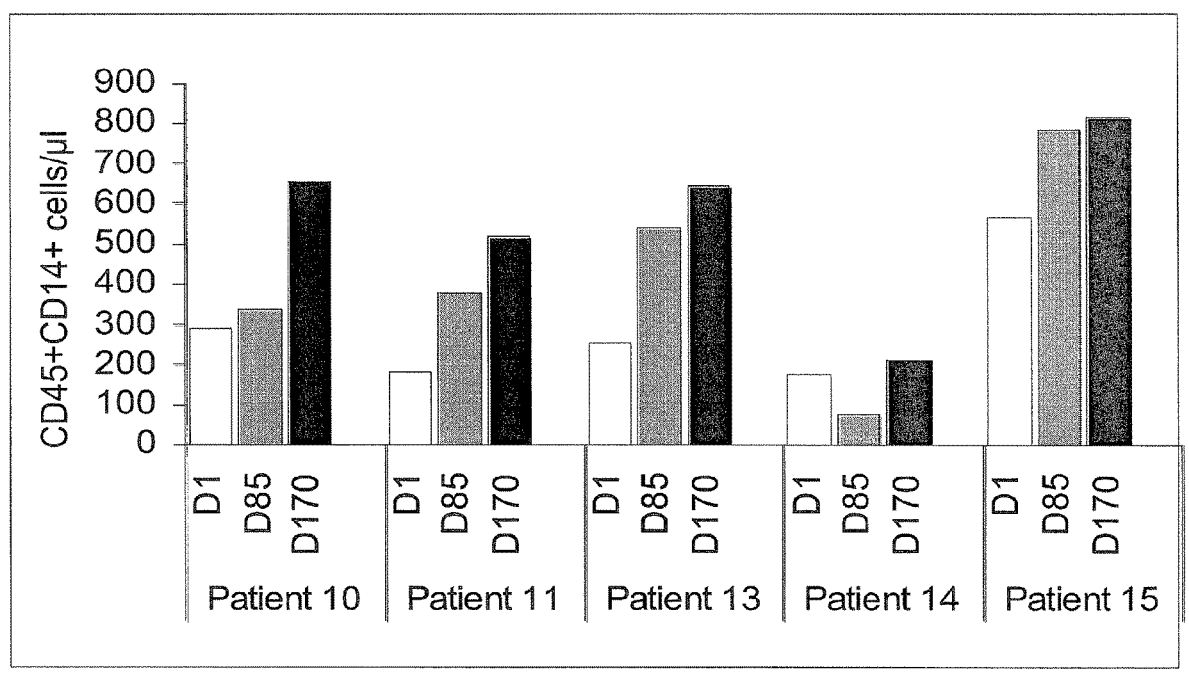
FIG. 4 represents fluorescence-activated cell sorting (FACS) analysis of monocytes (i.e. $CD14^+CD45^+$ cells) in fresh whole blood from metastatic breast carcinoma patients.

The results obtained in patients injected with a low dose IMP321 (1.25 mg) are represented in FIG. 4.

These data showed that doses of 1.25 mg in most if not all patients (FIG. 4) induce an expansion of the monocyte subset pool in the blood.

It is predicted that the optimal dose regimen for IMP321 will be between 6 and 30 mg/injection.

Figure 5:
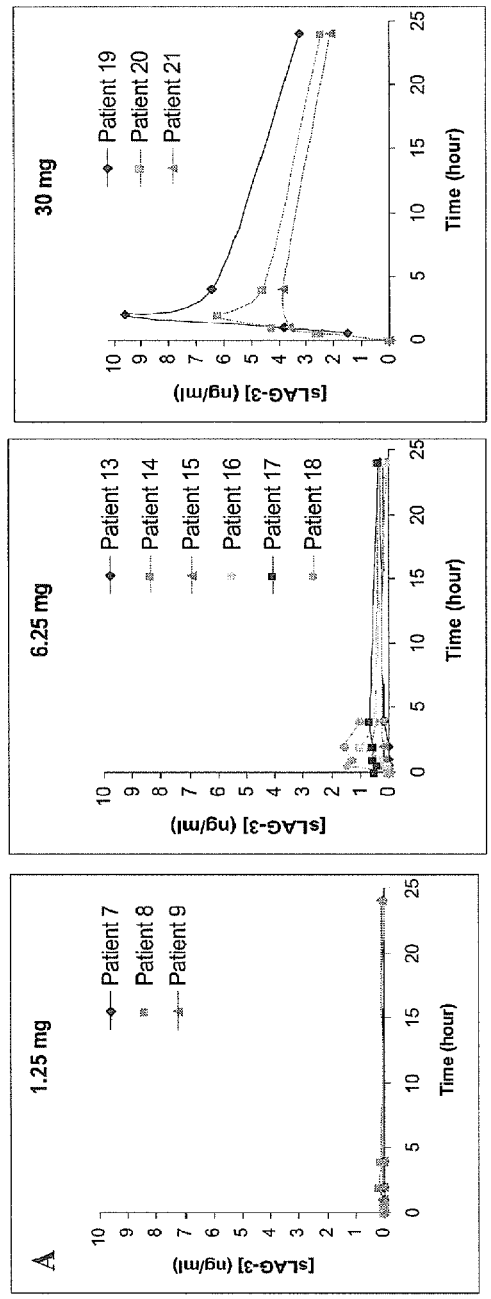
FIG. 5 represents the pharmacokinetic profiles of IMP321 measured by ELISA in the plasma of metastatic renal cell cancer patients.

These doses have been shown to be safe and give an acceptable systemic exposure based on the results of pharmacokinetics data obtained in metastatic renal cell cancer patients (FIG. 5). A blood concentration of IMP321 superior to 1 ng/ml for at least 24 hours after s.c. injection could be obtained in patients injected by IMP321 doses of more than 6 mg (FIG. 5).

Example 4: Treatment of Advanced Pancreas Cancer Patients Receiving Gemcitabine and IMP321 Doses Patients, receiving as a first line chemotherapy for advanced pancreas cancer (or patients not eligible for surgical removal of the tumor) 6 cycles of standard gemcitabine (1 gm/m$^2$ given i.v. over 30 min) on days 1, 8, and 15 of a 28 day cycle, receive in addition 6 to 30 mg s.c. IMP321 on days 2 and 16 of each 28-day cycle. Alternatively, IMP321 is administered at days 3 or 17.

Accordingly, each patient receives a standard 6-month course of gemcitabine with 12 s.c. injections of IMP321, each injection being given one to two days after gemcitabine administration on an every-two-week schedule.

The number of monocytes is analysed by fluorescence-activated cell sorting (FACS) as in example 1.

Example 5: Induction of Increased Rituximab-Mediated ADCC by Low Doses IMP321

PBMCs are first incubated for 40 hours with IL-2 (100 U/ml), with or without IMP321 (at the concentrations 0 μg/m, 0.03 μg/ml or 0.1 μg/ml). PBMCs are then incubated with increasing concentrations of rituximab (0, 0.5 and 5 μg/ml) in the presence of target cells (i.e. human CD20$^+$ Raji B cells).

Raji cells were first labeled with CFSE (carboxy-fluorescein succinimidyl ester), incubated in medium with rituximab at 0, 0.5 or 5 μg/ml and cocultured with effector cells at an effector-target ratio of 25:1 for 6 hours at 37° C.

The cells were then incubated with 7-AAD (7-aminoactinomycin-D) for 15 min on ice and analyzed by flow cytometry to determine the percentage of dead CFSE$^+$7-AAD$^+$ Raji target cells (i.e. % of cytotoxicity).

Figure 6:
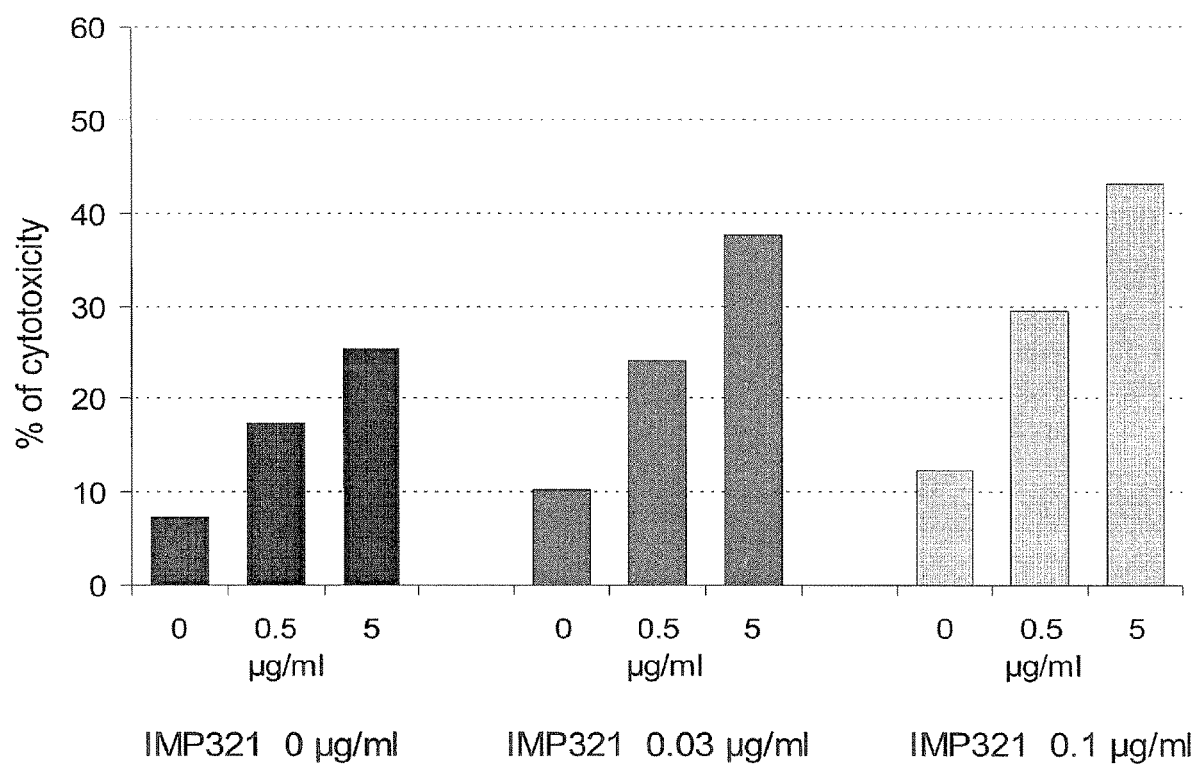
FIG. 6 represents the flow cytometry analysis of PBMC cultured in different conditions with rituximab and/or IMP321.

The results are presented in FIG. 6.

Increasing the concentration of rituximab increased the percentage of cytotoxicity, clearly showing a dose-dependent ADCC activity.

When 0.03 or 0.1 μg/ml IMP321 is added, the percentage of cytotoxicity greatly increased. For instance, a 30% cytotoxicity is observed with 0.5 μg/ml rituximab in the presence of 0.1 μg/ml IMP321 which is superior to the 25% cytotoxicity value obtained with 5 μg/ml rituximab in the absence of IMP321.

Thus, adding 0.1 μg/ml IMP321 potentializes 10-15 fold the activity of rituximab because a superior cytotoxicity is obtained with 10 time less antibody when a low dose IMP321 (0.1 μg/ml) is added.

These data show the synergistic effect between rituximab and IMP321.

REFERENCE LIST

[1] TRIEBEL et al., J. Exp. Med., 171: 1393-1405, 1990
[2] BRIGNONE et al., J. Immune Based Ther Immunotherapies, 5: 5, 2007
[3] TRIEBEL et al., Trends Immunol., 24: 619-622, 2003
[4] HUARD et al., Proc. Natl. Acad. Sci. USA, 94: 5744-5749, 1997
[5] PRIGENT et al., Eur. J. Immunol., 29: 3867-3876, 1999
[6] BRIGNONE et al., J. Immunol., 179: 4202-4211, 2007

The invention claimed is:

1. A method of treating cancer in a human subject in need thereof, which comprises:
   administering to the subject an effective amount of:
   (i) a chemotherapy agent; and
   (ii) IMP321;
   wherein the IMP321 induces a systemic increase in the number of monocytes in blood of the subject, and elicits a systemic monocyte-mediated immune response;
   wherein the IMP321 is administered to the subject at a dose of more than 6 mg; and
   wherein the blood concentration of the IMP321 in the subject is greater than 1 ng/ml, for at least 24 hours after administration of the IMP321 to the subject.

2. The method of claim 1, wherein the chemotherapy agent and the IMP321 are administered to the subject simultaneously, separately, or sequentially.

3. The method of claim 1, wherein the IMP321 is administered 12 to 96 hours after administration of the chemotherapy agent.

4. The method of claim 1, wherein the subject is treated without administration of any additional antigen.

5. The method of claim 1, wherein the subject is administered an effective plurality of doses of the IMP321.

6. The method of claim 1, wherein the cancer is metastatic breast cancer or metastatic renal cell cancer.

7. The method of claim 1, wherein the chemotherapy agent is selected from the group consisting of taxanes, anthracyclines, and gemcitabine.

8. The method of claim 7, wherein the chemotherapy agent is a taxane.

9. The method of claim 8, wherein the taxane is paclitaxel.

10. The method of claim 1, wherein the IMP321 is administered to the subject at a dose of more than 6.25 mg.

11. The method of claim 1, wherein the IMP321 is administered to the subject at a dose of about 30 mg.

* * * * *